(12) United States Patent
Ferro et al.

(10) Patent No.: US 10,568,615 B2
(45) Date of Patent: Feb. 25, 2020

(54) SURGICAL DEVICE

(71) Applicant: AOD HOLDINGS, LLC, Arroyo Grande, CA (US)

(72) Inventors: Thomas D. Ferro, Arroyo Grande, CA (US); Joe Phillips, Paso Robles, CA (US); Austin Ferro, Arroyo Grande, CA (US); Donald Lee, San Luis Obispo, CA (US)

(73) Assignee: AOD Holding, LLC, Arroyo Grande, CA (US)

( * ) Notice: Subject to any disclaimer, the term of this patent is extended or adjusted under 35 U.S.C. 154(b) by 165 days.

(21) Appl. No.: 15/206,584

(22) Filed: Jul. 11, 2016

(65) Prior Publication Data

US 2017/0007225 A1   Jan. 12, 2017

Related U.S. Application Data

(60) Provisional application No. 62/178,765, filed on Jul. 10, 2015.

(51) Int. Cl.

| A61B 17/66 | (2006.01) |
|---|---|
| A61B 17/02 | (2006.01) |
| A61B 1/32 | (2006.01) |
| A61F 2/38 | (2006.01) |
| A61B 17/15 | (2006.01) |

(52) U.S. Cl.
CPC .............. *A61B 17/025* (2013.01); *A61B 1/32* (2013.01); *A61B 17/155* (2013.01); *A61B 17/157* (2013.01); *A61F 2/38* (2013.01); *A61B 2017/0268* (2013.01)

(58) Field of Classification Search
CPC .......... A61B 17/025; A61B 2017/0268; A61B 17/154; A61B 17/157; A61B 17/155
USPC .......................................................... 606/88
See application file for complete search history.

(56) References Cited

U.S. PATENT DOCUMENTS

| 5,669,914 A * | 9/1997 | Eckhoff ............... A61B 17/157 606/102 |
|---|---|---|
| 2004/0097951 A1* | 5/2004 | Steffensmeier ........ A61B 5/107 606/102 |
| 2004/0167531 A1* | 8/2004 | Hodorek .............. A61B 17/157 606/87 |
| 2009/0270869 A1* | 10/2009 | Colquhoun .......... A61B 17/025 606/88 |
| 2010/0100102 A1* | 4/2010 | Duggineni ........... A61B 17/025 606/102 |
| 2010/0249789 A1* | 9/2010 | Rock .................. A61B 17/0206 606/88 |
| 2013/0165939 A1* | 6/2013 | Ries ................... A61B 17/8863 606/88 |

* cited by examiner

*Primary Examiner* — Matthew J Lawson
(74) *Attorney, Agent, or Firm* — McDonnell Boehnen Hulbert & Berghoff LLP

(57) ABSTRACT

A surgical device is presented that combines multiple components and functions, such as, joint distraction, soft tissue distraction, a separation force that exerts a uniform tension on the knee ligaments, pre-aligned cut guides, and posterior cut guards that protect the posterior knee joint from unintentional damage by the surgical saw. A method of performing a partial knee replacement is also presented.

7 Claims, 3 Drawing Sheets

SURGICAL DEVICE

CROSS REFERENCE TO RELATED APPLICATIONS

The present application is a non-provisional application of U.S. Provisional Patent Application No. 62/178,765, filed Jul. 10, 2015. The entire disclosure contents of this application is herewith incorporated by reference into the present application.

FIELD OF INVENTION

The present invention relates to knee arthroplasty, and in particular, to an instrument and a minimally invasive method for preparing a knee joint to receive the components of a knee prosthesis. More particularly, the invention is related to a surgical device to perform unicompartmental knee replacement or "partial" knee replacement.

BACKGROUND

Orthopedic procedures for the replacement of all, or a portion of, a patient's joint have been developed over the last thirty years. In unicompartmental knee replacement (also called "partial" knee replacement) only a portion of the knee is resurfaced. This procedure is an alternative to total knee replacement for patients whose disease is limited to just one area of the knee. Because a partial knee replacement is done through a smaller incision, patients usually spend less time in the hospital and return to normal activities sooner than total knee replacement patients.

Currently, the procedures used to prepare the bone and seat the implants are generally referred to as open procedures. For the purposes of this discussion, the term "open procedure" will refer to a procedure wherein an incision is made through the skin and underlying tissue to fully expose a large portion of the particular joint surface. In both total and unicompartmental knee arthroplasty, the typical incision for an open procedure is about 8-10 inches long. After the initial incision in the skin, the internal wound may be enlarged to fully expose the areas to be prepared. While this approach provides surgeons with an excellent view of the bone surface, the underlying damage to the soft tissue, including the muscles can lengthen a patient's rehabilitation time after surgery. While the implants may be well fixed at the time of surgery, it may be several weeks or perhaps months before the tissues violated during surgery are fully healed.

With the above in mind the surgeon strives to perform surgery using minimally invasive procedures to reduce both the incision size and the damage to soft tissue, thereby shortening a patient's rehabilitation time. Partial knee replacement procedures generally involve the consecutive steps of making an incision and exposing the joint, resecting the distal end of the femur, resecting the proximal end of the tibia, sizing the femur and establishing external rotation, finishing the femur, sizing and finishing the tibia, performing trial reductions, and implanting the prosthesis components. Although effective, it is known that the joint space within which the surgeon must work is restricted and the cutting and removal of bone can be a challenging task when working in this small joint space.

Accordingly, there is a need for a method and an instrument that can be used to create additional space at the surgical site and facilitate the steps in the preparation of the knee joint to receive the components of a knee prosthesis. As described in detail below, the presently disclosed invention eliminates many of the known problems by combining cut operations and also providing fixed reference points for mounting of the cutting guides.

SUMMARY

This disclosure is directed to a multi-functional surgical device containing orthopedic cut guides and a method of using the surgical device that provides a means to distract the affected compartment of the knee, while positioning the required cut guides in the proper position to make the tibial plateau resection, as well as the initial femoral plateau resection cut. Another important aspect of the present disclosure in terms of the functioning of the surgical device is that it creates and maintains symmetrical spaces or "gaps" between the bones after the cuts are made. To ensure this, after squeezing the handles and applying a desired tensioning force to the ligaments, the cutting surfaces must be adjusted on the femoral side to a fixed distance between the two cut surfaces. This results in a fixed and perfectly rectangular gap, or space that is left between the femur & tibia bones after the cuts have been made.

The surgical device also combines joint distraction and soft tissue distraction with pre-aligned cut guides. The soft tissue retraction extends deep into the posterior aspect of the synovium that would otherwise be hard to place with existing orthopedic devices and would end up being a hindrance to the surgical procedure. The surgical device further provides a means of protecting the posterior knee joint from unintentional damage by the surgical saw through the application of integrated cutting guards in the device. The integral retractors of the surgical device that are built into the device not only help push soft tissue out of the cutting areas, but also assist in naturally positioning the cut guides of the surgical device by utilizing elliptical shaped retractor soft tissue retractors.

The surgical device also has a set of handles that when squeezed or closed can apply a separation force within the joint space between the distal end of the femur and the proximal end of the tibia. This movement of the handles will cause the top and bottom jaws or spreader bases of the surgical device to separate the knee, i.e., movement of the femur and the tibia relative to each other. This separation force creates a uniform tension on the knee ligaments and provides a passage way for the surgical saw to pass through without impinging on non-intended parts of the knee. By passing the surgical saw through the cut guides of the surgical device described herein, cuts can be made that more closely reference the individual patient's bone structure, as well as the patient's individual ligament morphology.

Accordingly, one embodiment of the invention concerns a surgical device comprising a first handle and a second handle that are pivotally connected to one another and spaced a distance H apart in a first initial position. A first spreader base is connected to the first handle and a second spreader base is connected to the second handle, where the first and second spreader bases are separated by a distance S. At least one tissue retractor is connected to either the first spreader base or the second spreader base and a cut guide is connected to either the first or the second spreader base.

The surgical device can be configured such that movement of the first handle and the second handle to a second position decreases the distance H and causes the distance S to increase thereby moving the first and second spreader bases further apart from each other.

The surgical device can also have at least two cut guides, where a first cut guide is attached to the first spreader base and a second cut guide is attached to the second spreader base. These cut guides are configured to accept one or more surgical saw blades to perform resection of the tibia and the femur in a partial knee replacement surgery.

The surgical device can also have at least two soft tissue retractors, preferably elliptically shaped, where a first retractor is attached to the first spreader base and a second retractor is attached to the second spreader base. One or more gripping surfaces are located on either the first spreader base or the second spreader base or both. In order to protect against unwanted or accidental cutting of the joint's capsule tissue or nerve bundle, the surgical device can include one or more posterior cut guards.

The present disclosure also involves a method of performing a unicompartmental knee replacement of a knee joint comprising making an incision in a knee near the knee joint to expose the femur and tibia, inserting the surgical device of described above between the tibia and the femur, squeezing or closing the first and second handles together to decrease the distance H in order to generate a separation or traction force that causes both joint distraction and soft tissue distraction. This separation force causes the tibia and femur to separate such that the a surgical saw can be inserted into the cut guide and used to resect the tibia or the femur or both. Once the necessary resections are performed a partial joint replacement device or implant is fixedly attached to the resected bones.

DETAILED DESCRIPTION

Figure 1:
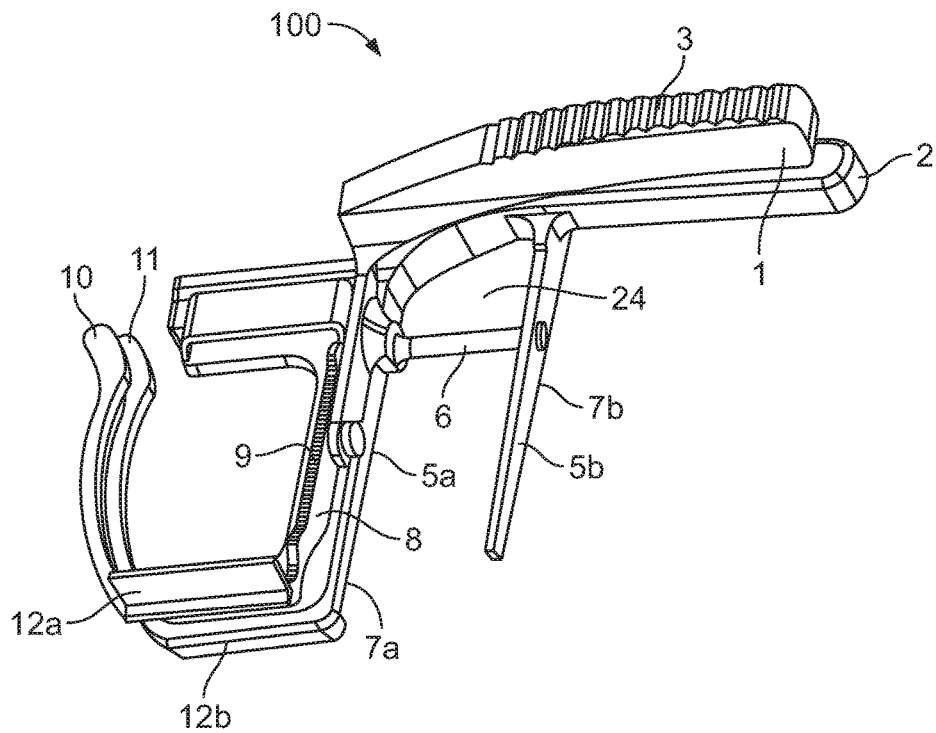
FIG. 1 shows a perspective view of the surgical device of the instant disclosure.
Figure 2:
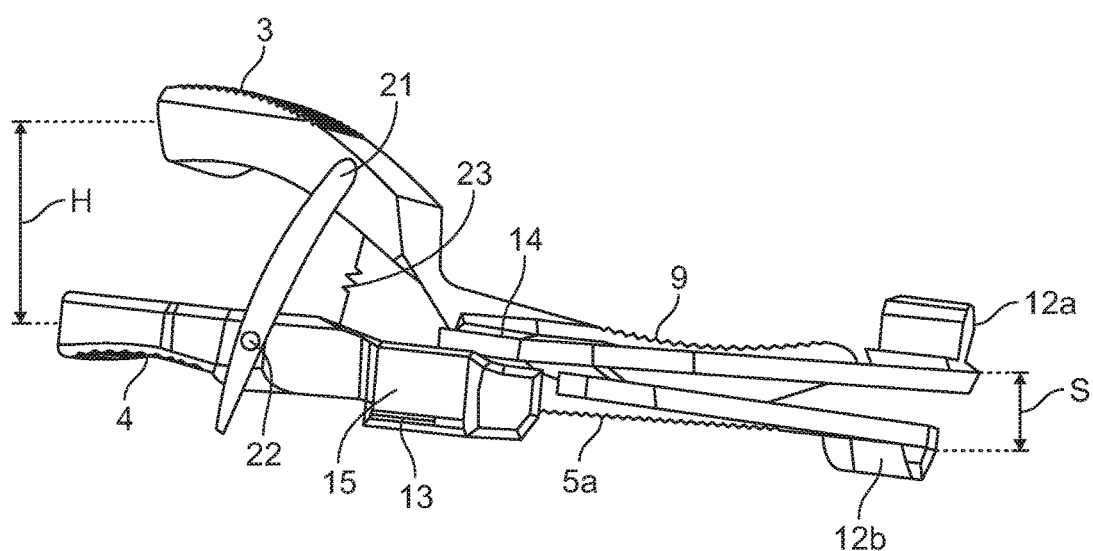
FIG. 2 shows another perspective of the surgical device of FIG. 1 where the handles are in an open position and the spreader bases are in a closed or initial position.
Figure 3:
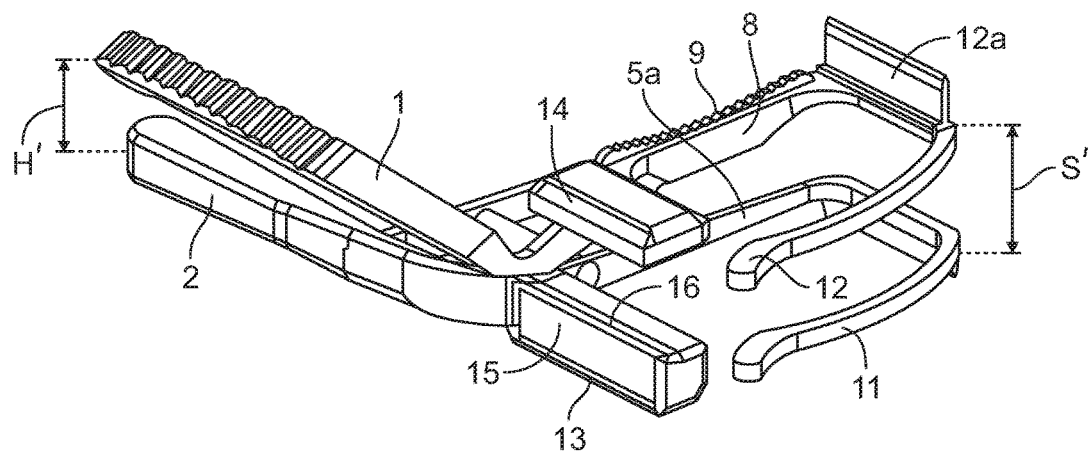
FIG. 3 shows yet another perspective of the surgical device of FIG. 1 where the handles are in a closed or partial closed position and the spreader bases are in an extended or open position.

Reference is now made to FIGS. 1-3. The surgical device 100 of the present disclosure provides a multitude of functions to assist a surgeon during a partial knee replacement. More specifically, the surgical device disclosed herein provides at least the following features:

joint distraction, i.e., extending the space between the tibia and the femoral condyle;

soft tissue distraction around the knee joint, i.e., pushing the synovium and related soft tissue out of the way to clearly expose the knee joint;

providing a separation force that exerts a uniform tension on the knee ligaments and provides a passage way for the surgical saw to pass through without impinging on non-intended parts of the knee;

pre-aligned cut guides to ensure accurate resection of the femoral condyle and the tibia; and posterior cut guards that protect the posterior knee joint from unintentional damage by the surgical saw, more specifically to protect the vital nerve bundles and posterior joint capsule from inadvertent cuts.

Handles 1 and 2 are pivotally connected through pivot 6, which bridges a U-shaped region 24 that is used as a reference for notch and ACL attachment point. This region guides precise medial-lateral (side-to-side) and correct rotational placement of the cutting guides. It also assists in correct implant sizing. The handles are initially separated by a distance H. Optionally the handles can be connected to a locking mechanism so that when the handles are squeezed to closed position, where the distance between the handles is less than H, the handles can be releasably locked in position. One possibly way to accomplished this locking feature is shown in FIG. 2 where a locking mechanism comprises a bracket 21 connected to one of the handle that is configured to move relative to the other handle. Once the handles are squeezed and moved to the desired position the handles are locked in position relative to each other by means of a set screw 22. Alternatively, a releasable ratchet, a cam-lock, a rack & pinion system, or the like locking mechanisms could be used. Maintaining the distraction of the joint and/or limiting this distraction with a clutch or any such mechanism that prevents forces above a set value during the distraction process is desirable. Strain gauge 23, Wheatstone bridge or any like measuring system, direct or indirect, can be used to accurately measure the forces applied to the ligaments when setting the bone distraction could also be used when the handles are moved to a more closed position.

Connected to each handle is a spreader base. In the embodiment shown in FIGS. 1-3 handle 1 is connected to a first spreader base 8 and handle 2 is connected to a second spreader base 5*a*, 5*b*. This second spreader base has two laterally spaced apart spreaders 5*a* and 5*b* that work in unison, meaning that they both move together simultaneously when handle 2 is moved. The surgical device 100 works in a manner opposite that of a common pair of scissors. In other words, when the handles are in an open or initial position, the spreaders 8, 5*a*, & 5*b* are in a closed or ready position. And, when the handles are squeezed together the spreaders open or move away from each other.

Each of the spreaders has a gripping surface associated with it, preferably in the form of a serrated set of sharp teeth that will positively engage the knee joint bones without slippage during retraction or separation of the femur from the tibia. The first spreader base 8 has gripping surface 9 (serrated femoral engagement surface) and the two spreaders 5*a*, 5*b* of the second spreader base each have gripping surface 7*a* and 7*b* (serrated tibial engagement), respectively. In addition, these gripping surfaces are useful after bone cutting to assist in precise maintenance of distraction force during installation of the implant.

Connected to each of the spreader bases are guide guides 13, 14, 15 and 16. More specifically, the second spreader base has cut guide 15 that comprises two cutting guides 13 and 16, where cut guide 13 allows for tibial resection and limits the lateral excursion of the surgical saw blade, thus limiting the depth of cut because the saw will bottom out on the front surface of the guide to protect the posterior structures in the knee. Cut guide 16 is for the vertical tibial resection and is configured to provide precise rotation and positional guidance while limiting vertical excursion of the surgical blade up & down. This resection is a short vertical cut in the tibia that is required to inset the tibial component of the knee replacement implant. Cut guide 16 also limits the depth of cut because the saw bottoms out on the front of the guide thus protecting the posterior structures in the knee. It is within the scope of this disclosure that guide 16 may be substituted for other types of guides, for example, a drill guide to provide for a rounded corner to prevent formation of a stress riser at the corner. Cut guide 14 allows for a femoral resection cut and provides for precise guidance of the saw blade and limits lateral excursion and depth of cut by causing the saw blade to bottom out on the front of the guide. Again, this protects the posterior structures in the knee.

Each spreader base may also have a posterior cut guard. The embodiment shown in the figures show a first posterior cut guard 12a associated with the first spreader base 8 and a second posterior cut guard 12b associated with the second spreader base 5a, 5b. These cut guards prevent the surgical saw from extending past the bone into the soft tissue and also help position the cutting guides described above by locking against the back (posterior margin) of the femur above and the tibia below.

The spreader bases also can include soft tissue retractors 10 and 11. These tissue retractors protect MCL (medial collateral ligament) and capsule & skin and other soft tissue. Additionally, these retractors provide the surgeon needed visual access to the knee joint during bone resection. They also provide tension on medial structures to assist in lining bones up for cuts so as to result in symmetrical, rectangular flexion and extension gaps.

Figure 4:
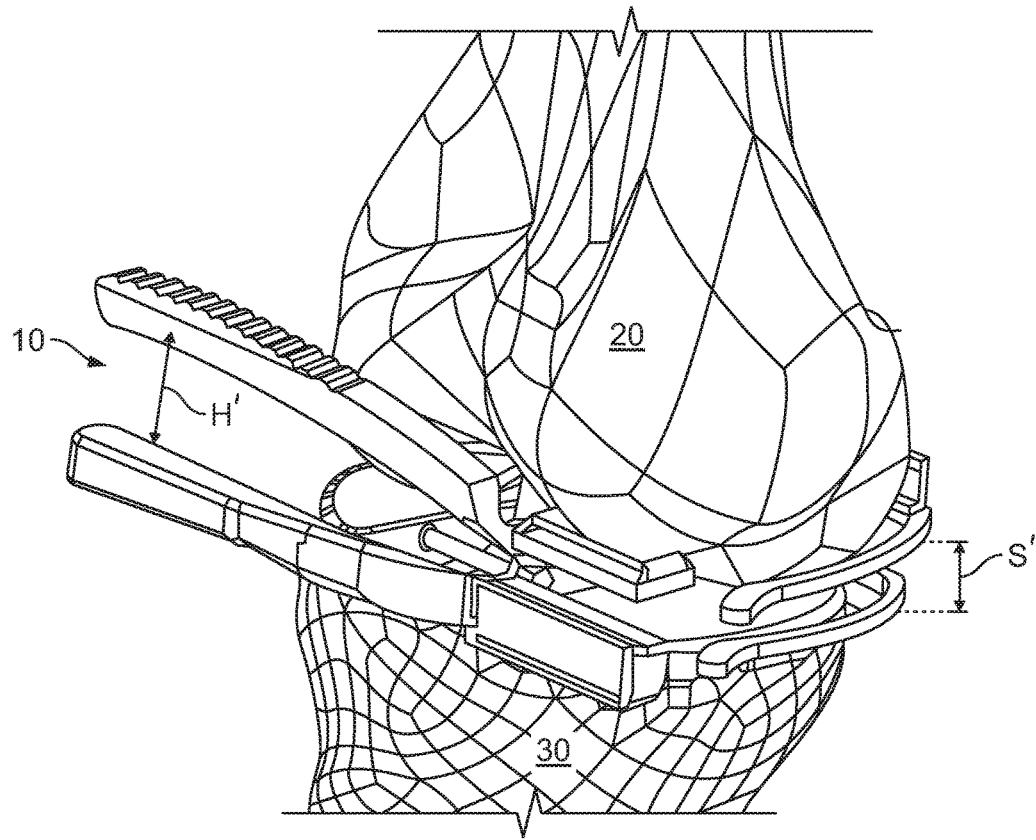
FIG. 4 shows another perspective view of the surgical device of FIG. 1 inserted between the femur and the tibia and providing a tensioning force to separate the femur and the tibia from each other.
Figure 5:
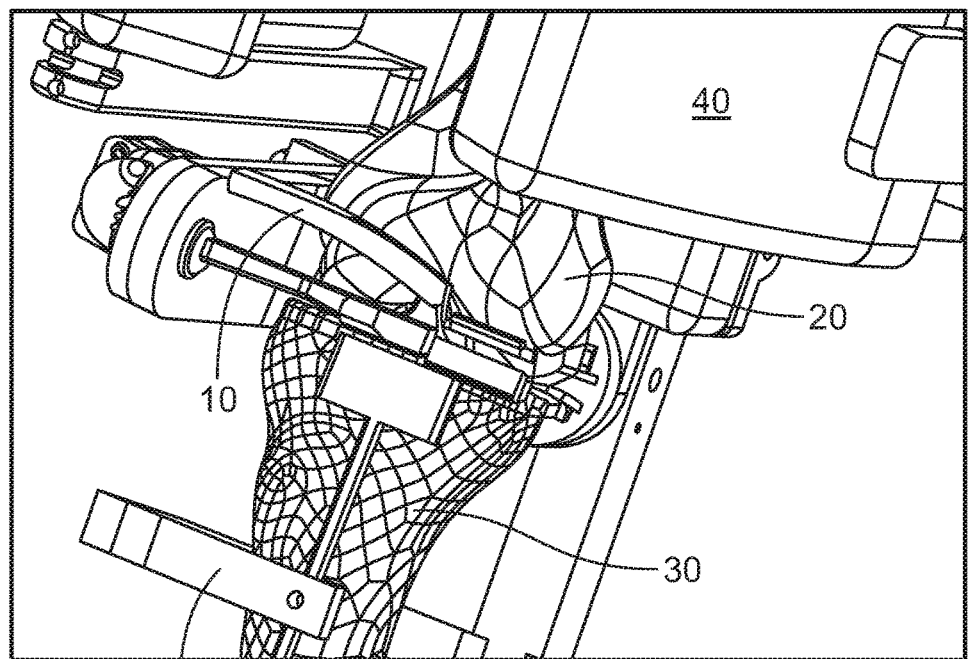
FIG. 5 shows a perspective view of the surgical device of the present invention attached to an optional leg holder device and inserted between the femur and the tibia.
Figure 6:
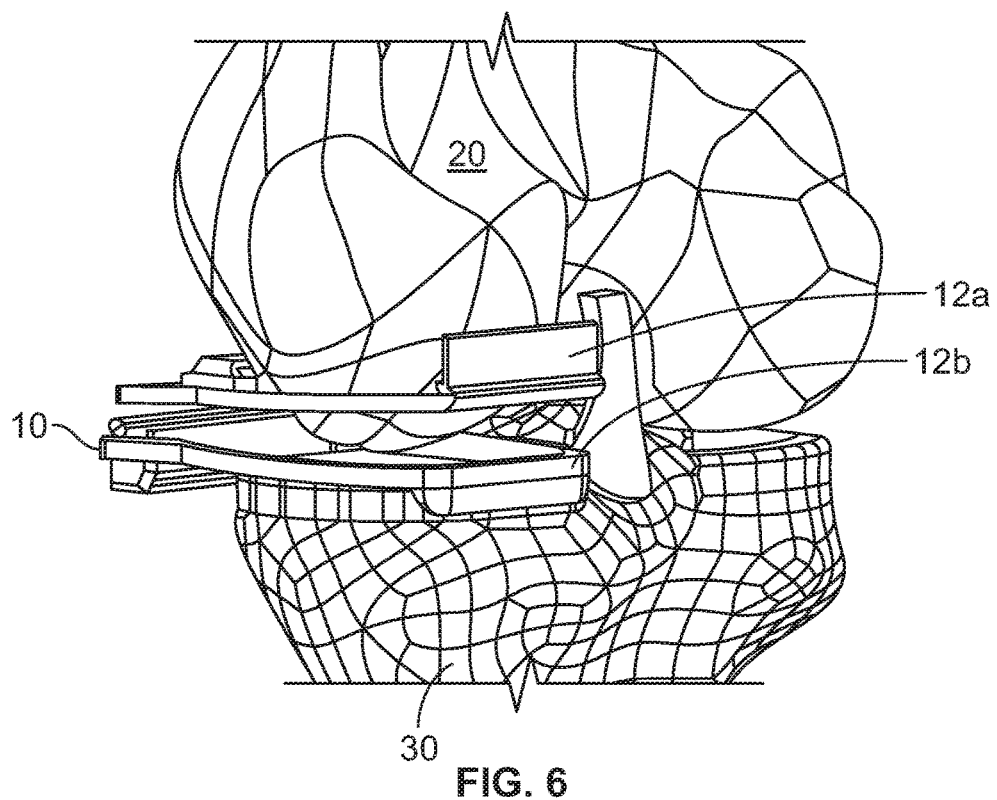
FIG. 6 shows a perspective posterior view of the surgical device of the present invention inserted between the femur and the tibia and the posterior cut guards.

Turning next to FIG. 4, there is shown the surgical device 100 inserted between femur 20 and tibia 30. Device 100 is shown in a tensioned position where the handles are squeezed such the distance between the handles are H', which is less than H, and where the two spreader bases have moved to a distance S' further from one another, where S' is greater than S. In this tensioned position there is joint distraction where the two spreader bases are exerting a separation force that provides a tension on the ligaments in the knee. Prior to closing the handles the surgical device is rotationally and translationally movable by the surgeon to position the device to match the patients anatomy precisely. The surgical device 100 can also be employed as part of a system as shown in FIG. 5 where it is integrated with and attached to a leg holding device 40 through mount 41. Such a system increases operating room efficiency by decreasing redundant steps of positioning, increases accuracy of the resections because the leg is well fixed in the leg holding device and allows for incorporation of other surgical devices needed as part of the knee replacement procedure.

The surgical device 100 can be fabricated out a variety of materials, including metal and plastics. In some cases, it may be desirable to fabricate some parts out of a translucent or semi-translucent material (polycarbonate, ethymethacrolate, or any similar material, or incorporates such or any type of fiber optic lighting structures or focused light source, so as to provide illumination within the cavity of the knee during use of the device. Any or all parts of the device can be disposable and or recyclable, including all concepts related to translucency and/or incorporating lighting considerations, and constructed specifically to accommodate materials that lend themselves to such, to be produced and distributed in "factory" (off site from the hospital or ASC (ambulatory surgical center) sterilized sealed packages providing a higher level of sterility (ethylene oxide gas sterilization or gamma irradiation, for example, performed in/through hermetically seal containers, provide far superior sterility compared to hospital autoclave systems) and increased convenience/economy/efficiency to the end user.

One possible method of use of the surgical device 100 will now be described in the context of a partial knee replacement. First, an incision is made in the knee to provide surgical access to the affected joint. The femur and tibia are exposed and initial visual gauging and measurement will commence. The patient's leg is held in an extended position. Once this is done, the surgical device 100 is inserted into the joint in its compressed or initial state with the handle a distance H apart. In this compressed state the spreader bases exhibit a small profile allowing them to pass through the narrow joint space between the tibia and the femoral condyle. As the device is inserted, the spreader bases on the sides of the both the femoral and tibial chassis will both aid in pushing the synovium and related soft tissue out of the way, and also act as a guide to help hold and locate the device within the joint capsule. The surgical device can be located either by visual reference of the patient's anatomical markers, or by way of mounting to a leg brace as described above. Once completed inserted between the tibia and femur, the next step is to apply a traction force to the joint by causing the two spreader bases to move apart through squeezing the handles together.

By squeezing the handles, the joint is compelled to separate, creating both clearances for the surgical saw, as well as placing uniform tension on the ligaments. This uniform tension will assist the surgeon in sizing and placing the knee implant in such a way that it best represents the patient's existing articular joint geometry. With the surgical device 100 in place, and the device is sufficiently distracted, the surgeon can make the needed bone cuts. After the removal of bone tissue, the knee can be flexed to 90 degrees and the posterior cut can be made. This posterior cut will be made with the femoral aspect of the cut guide, and it will be made while the device is maintained in its distraction mode. Once bone resection is complete the knee replacements are then installed in the tibia and femur.

The invention claimed is:

1. A surgical device comprising:
   a first handle and a second handle pivotally connected and spaced a distance H apart in a first initial position;
   a first spreader base connected to the first handle and having a gripping surface comprising a set of serrated teeth;
   a second spreader base connected to the second handle comprising two spreaders each having two gripping surfaces, where the two spreaders are connected through a pivot that defines a U-shaped region that is used as a reference for notch and ACL attachment, where the first and second spreader bases are separated by a distance S;
   a soft tissue retractor integral with either the first spreader base or the second spreader base, where the soft tissue retractor is elliptically shaped;
   a cut guide integral with either the first or the second spreader base, where the cut guide is pre-aligned having a fixed orientation relative to either the first or the second spreader base,
   wherein the first handle, the second handle, the first spreader, the second spreader, the soft tissue retractor and the cut guide are all integral parts of a single surgical device, where the cut guide is an integral part of the second spreader base when the surgical device is used to distract a joint or soft tissue.

2. The surgical device of claim 1 wherein movement of the first handle and the second handle to a second position decreases the distance H and causes the distance S to increase.

3. The surgical device of claim 1 further comprising an additional cut guide, where the cut guide is attached to the first spreader base and the additional cut guide is attached to the second spreader base.

4. The surgical device of claim 1 further comprising an additional soft tissue retractor, where the soft tissue retractor is attached to the first spreader base and the additional soft tissue retractor is attached to the second spreader base, where the additional soft tissue extractor has an elliptical shape that matches the elliptical shape of the soft tissue retractor.

5. The surgical device of claim 1 further comprising a gripping surface on either the first spreader base or the second spreader base.

6. The surgical device of claim 1 further comprising a posterior cut guard integral with the first spreader base.

7. A method of performing a unicompartmental knee replacement of a knee joint comprising:
   making an incision in a knee near the knee joint to expose the femur and tibia;
   inserting the surgical device of claim 1 between the tibia and the femur;
   squeezing the first and second handles to decrease the distance H to generate a separation force that causes both joint distraction and soft tissue distraction, where the tibia and femur are separated;
   inserting a surgical saw in the cut guide and resecting the tibia; and
   inserting a partial joint replacement device.

* * * * *